(12) United States Patent
Tomasgaard et al.

(10) Patent No.: US 6,858,658 B2
(45) Date of Patent: Feb. 22, 2005

(54) GRANULATED CUPROUS OXIDE FOR ANTIFOULING COATINGS

(75) Inventors: Lars Tomasgaard, Drøbak (NO); Jarle Ringseth, Bærumsverk (NO); Anders Bergkvist, Oslo (NO)

(73) Assignee: Nordox Industrier AS, Oslo (NO)

( * ) Notice: Subject to any disclaimer, the term of this patent is extended or adjusted under 35 U.S.C. 154(b) by 160 days.

(21) Appl. No.: 10/292,438

(22) Filed: Nov. 13, 2002

(65) Prior Publication Data

US 2004/0091550 A1 May 13, 2004

(51) Int. Cl.$^7$ .............................. C08K 3/10; C08K 3/18; C08K 3/22
(52) U.S. Cl. ....................... 523/122; 523/177; 524/413; 524/430
(58) Field of Search ................................ 523/122, 177; 524/413, 430

(56) References Cited

FOREIGN PATENT DOCUMENTS

| DE | 197 27 244 A1 | 12/1997 |
|----|---------------|---------|
| EP | 0 254 164 A1  | 1/1988  |
| EP | 0 480 614 A1  | 4/1992  |
| EP | 0 506 470 A1  | 9/1992  |
| GB | 685137        | 12/1952 |
| GB | 992646        | 5/1965  |
| WO | 00/60942      | 10/2000 |
| WO | 01/08494 A1   | 2/2001  |
| WO | 03/000054 A1  | 1/2003  |

*Primary Examiner*—Kriellion A. Sanders
(74) *Attorney, Agent, or Firm*—Young & Thompson

(57) ABSTRACT

The invention relates to granulated copper oxide containing a binding agent which is resistant to organic solvents, a process of preparing the material and the use thereof. This granulated copper oxide is highly suitable as a biocide in antifouling paints.

12 Claims, 2 Drawing Sheets

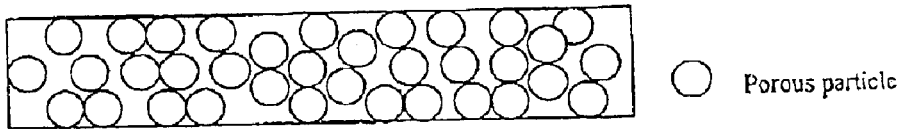
Figure 1. Paint film with granulated cuprous oxide.
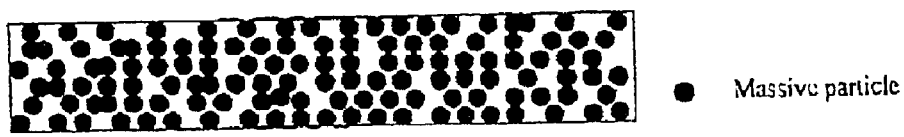
Figure 2. Paint film with standard cuprous oxide.
Figure 3. Paint film with cuprous oxide and filler after some time in water. The paint film is partly eroded/polished.
Figure 4. Paint film with cuprous oxide after some time in water. The paint film is partly eroded/polished.

Figure 5. Painted steel sheets with, from left to right, XLT-G, PG and LoLo Tint.
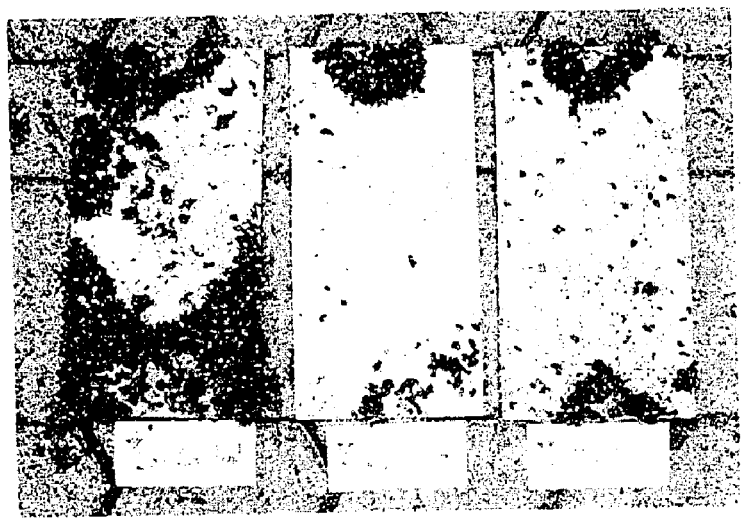
Figure 6. Painted steel sheets after exposure in sea water for two months.

GRANULATED CUPROUS OXIDE FOR ANTIFOULING COATINGS

FIELD OF THE INVENTION

The present invention relates to a Cu-containing material for biocide applications, a process of preparing such a material and the use of the material as a biocide in antifouling coatings.

BACKGROUND OF THE INVENTION

A purpose of biocides is to prevent the deposition of organic material on different constructions and is often mixed in a suspension (paint) which is applied on the constructions. The mode of performance comprises slow solution of the biocide active compound in water, and it is absorbed from this by simple organisms being present on or close to the surface resulting in intoxication.

Copper was among the first metals which were used in fouling preventive agents for marine applications in a large scale. In the ancient Egypt wooden boats were covered by copper plates to prevent fouling, and the British marine took the same method officially into use in 1762. By the change to steel ships in the nineteenth century it was observed that the copper plates experienced corrosion problems, and they were replaced with copper-containing antifouling. Copper powder, copper-brass powder, cupric hydroxide, cuprous oxide, cuprous thiocyanate and arsenite have all been used in antifouling to a varying extent. It is now generally accepted that cuprous oxide provides the best combination of efficiency, economy and ecological acceptability (H. Wayne Richardson (Ed.): "Handbook of Copper Compounds and Applications", Marcel Dekker, New York, 1997 (432 p)).

In the work discussed herein attention is paid to the advantages of cuprous oxide in the invention disclosed.

Cuprous oxide can be prepared by electrolysis, pyro-metallurgy or hydro-metallurgy (H. Wayne Richardson (Ed.): "Handbook of Copper Compounds and Applications", Marcel Dekker, New York, 1997 (432 p)).

Method 1: Copper is heated in the air to temperatures above 1030° C., wherein cuprous oxide is thermodynamically stable. A cooling must take place in an inert atmosphere to prevent further oxidation into cupric oxide. The method results in large lumps of copper oxide.

Method 2: Copper is oxidised in an autoclave at 120° C. and 6 atmospheres in the presence of water, air and small amounts of HCl and $H_2SO_4$. The method results in a variable size of particles and density, depending on the pressure and temperature in the reactor.

Method 3: Copper oxide is precipitated by mixing a dissolved copper salt (e.g. $Cu_2(NH_3)_4CO_3$ or CuCl) with NaOH in an aqueous solution. The method results in different particle sizes depending on pH and the temperature of the mixing step.

The efficiency of bioactive compounds depends on several factors: The specific copper compound, the dissolution rate of the copper compound and the persistence of the solution. For environmental reasons it is often desirable to achieve a slow dissolution of the copper compound. This may among others be obtained by increasing the circumference of the elemental particles, i.e. by reducing their total external surface. A reduction of the external surface has also another desirable effect: The particles will be colourless and can be used in paints of different colours.

A conventional copper oxide has elemental particles of a diameter in the range >5 µm. In the last years a new commercial product has entered the market having a diameter <10 µm under the name XLT (extra Low Tint). This product may be produced either through the powderisation of copper oxide prepared by high temperature oxidation or by thermal treatment (sintering) of small elemental particles. Both processes involve the use of temperatures in excess of 1000° C., which implies heavy demands as to the process equipment and materials. Further, both processes result in a variation of particle size and large, respectively small, particles have to be powderised, respectively sintered repeatedly after the first cycle to obtain a satisfying yield of the process.

The aim of the present invention was therefore to provide a product and a process which did not suffer from the above disadvantages.

SUMMARY OF THE INVENTION

This is achieved according to the instant invention by those features which appear from the characterizing clause of claim 1.

It is further preferable that one or more binding agents are added prior to the granulation.

Preferably one or more organic polymer compound is used as binding agent, particularly preferred one or more polymer alcohol is used as binding agent.

Particularly preferably polyvinylaclohol (PVA) and/or polybuthylalcohol (PBA) are used as binding agent, preferably polyvinylaclohol (PVA). PVA is delivered in several versions with respect to hydrolysation degree and therefore different water solubility. By varying the hydrolysation degree, the dissolution rate can be varied. This relation makes it possible to choose the dissolution profile of the cuprous oxide based on need of antifouling protection for a given type of water.

The contents of PVA as binding agent are preferably in the range of 0.3% to 8% calculated as percent by weight of the dried granules.

Preferably the material substantially comprises $Cu_2O$.

Further the invention provides for a process of preparing a $Cu_2O$ with a low strength of colour as defined above, wherein conventionally prepared $Cu_2O$ is added to one or several binding agents and thereafter granulated.

The main aim of the invention as disclosed herein was to prepare large particles of copper oxide without high temperature processing. Further it was an object to enable the preparation of particles having a porous structure and lower density than generic copper oxide and considerably lower than for conventional XLT. This will facilitate the floating in a suspension compared to conventional XLT. This means that the granulated copper oxide will be less apt to sedimentation and will result in much better handling properties.

The lower density will also facilitate the reduction of copper content in antifouling paints, which is illustrated in the enclosed figures (number 1 to 4). The figures illustrate a paint film with an original thickness of 100 µm.

The paint film will gradually be eroded and new copper oxide will gradually be exposed. This mechanism is important for most antifouling paints, both the eroding and the self polishing. Copper oxide acts not only as a biocide, but also as a filler. With large porous copper oxide granules (FIG. 1) less copper oxide is required to maintain the volume of the paint. FIG. 2 shows a principal sketch with standard copper oxide. Considering that standard copper oxide particles are massive (not porous), the concentration of copper will be higher to achieve the same paint volume/film thickness. An alternative to the porous particles would be to use filler. The use of filler would probably result in a rough surface when the paint including the copper oxide dissolves into the surrounding water. The filler, which does not dissolve, will give roughness as shown in FIG. 3.

The corresponding result with porous copper oxide will be as shown in FIG. 4. The granules will dissolve with approximately the same rate as the paint itself and will therefore give the paint a smoother surface during its lifespan.

In addition, the invention will because of high average particle size be almost free of dust. This will further result in better handling properties.

Preferably the granulation takes place in a spray dryer, particularly preferred a spray dryer having rotating nozzles.

Preferably an organic compound is used, preferably an organic polymer compound, most preferably a polymer alcohol and particularly polyvinyl alcohol (PVA) is used as the binding agent.

Finally the invention relates to the use of the material as defined above as a biocide.

Particularly it is used for the inhibition of fouling.

The main aim of the invention as disclosed herein was to prepare large particles of copper oxide without using conventional processes. Further it was an object to enable the preparation of particles having a well defined size and in addition a well defined outer surface. It was also an aim to enable the preparation of particles with dissolution properties that can be controlled and modified. These objects were obtained according to the invention by using a process wherein small elemental particles are granulated to the desired particle size with a binding agent which is sparingly soluble in water and resistant to the organic solvents which are used in paints. Further, it was found that that the product which is prepared according to the invention disclosed has a further advantage in the granulated particles including cavities. This will facilitate the floating in a suspension compared to conventional XLT.

DESCRIPTION OF FIGURES

FIG. 1 illustrates a paint film with granulated copper oxide in the shape of porous particles.

FIG. 2 illustrates a paint film with standard copper oxide in the shape of massive (not porous) particles.

FIG. 3 illustrates erosion/polishing of the paint film with standard copper oxide and filler after some time in water.

FIG. 4 illustrates erosion/polishing of the paint film with granulated copper oxide after some time in water.

FIG. 5 shows a colour test of paint containing the product according to the invention (XLT-G), Nordox PG and the product LoLo Tint from American Chemet as an active biocide.

FIG. 6 shows a fouling test after two months in seawater in the Oslofjord with the same products, however, in the reverse order from left to right.

TABLE 1

Examples of commercial copper oxide products and the granulated product according to the invention.

| Producer | Product | Bulk density (g/cc) | Oil absorption |
|---|---|---|---|
| American Chemet | LoLo Tint | 3.5 | 8.4 |
| American Chemet | Red Copp 97N | 2.8 | 9.1 |
| NORDOX Industrier AS | Cuprous Oxide Red | 2.2 | 11 |
| NORDOX Industrier AS | Granulated Cu(I)O | 1.1 | 4 |

The invention is illustrated by, but not limited to, the examples to follow.

EXAMPLES

General: The granulation tests were performed in a conventional spray drier having rotating nozzles. Particle size measurements were performed with laser scattering (Malvern Scirocco 2000). Colour analyses of coatings were performed by means of a Minolta CM-3500d spectrophotometer.

Different primary particles were used in the tests, see table 2. $D_{50}$ denotes average based on 50% of the particles being larger and 50% being smaller than $D_{50}$.

TABLE 2

| Name | Producer | $D_{50} \mu m$ |
|---|---|---|
| PG | Nordox Industrier AS | 3.2 |
| Agro | Nordox Industrier AS | 1.2 |
| LoLo Tint | American Chemet | 18 |

Example 1

Granulation of Copper Oxide with PVA as a Binding Agent

To wet cuprous oxide polyvinyl alcohol was added in the range of 0.3 to 8%, and the mixture was granulated in a spray drier with rotating nozzles. Two types of primary particles were tested; Agro with $D_{50}$ of 1.2 $\mu$m and PG with $D_{50}$ of 3.5 $\mu$m. The water contents of the mixture was in the range of 25 to 55% by weight. Particle sizes, measured before and after granulation, are shown in table 3.

TABLE 3

| Sample identity | Primary particle | Water content of slurry (%) | PVA (%) | Particle size of granules, $D_{50}$ ($\mu$m) |
|---|---|---|---|---|
| A | Agro | 40 | 5 | 31 |
| B | PG | 40 | 3.7 | 46 |
| C | PG | 45 | 2 | 46 |
| D | PG | 50 | 3.5 | 67 |
| E | PG | 55 | 4 | 69 |

Example 2

Colour and Antifouling Properties

Different versions of granulated cuprous oxide were mixed in paint formulated for use as antifouling.

The white base formulation consisted of:

- 800 g (26%) Commercial binder for antifouling paints (Vinyl solution)
- 1000 g (32%) $Ti_2O$
- 120 g (4%) Softener
- 20 g (1%) Gray Vallac
- 640 g (21%) Colofonium 80 g (3%) Shellsol
460 g (15%) Xylen The white base formulation was prepared in a high speed mixer at 3900 rpm for 20 minutes.

Antifouling paints were prepared by adding 100 g of cuprous oxide to 400 g white base formulation.

6 different cuprous oxides were tested for colour and antifouling properties. The paints were brought on to steel sheets approximately 20×30 cm and submerged in sea water (the Oslofjord) during one month in summer 2002. The results are listed in table 4 below. Slime means growth of green algae. Shell means growth of mussels.

TABLE 4

| Paint no. | $D_{50}$, μm | Granulation, name | Antifouling properties |
|---|---|---|---|
| 1 | Agro | Sample A, table 2 | Some slime |
| 2 | PG | None | Some slime |
| 3 | LoLo Tint | None | Some slime and some shell |
| 4 | PG | Sample C, table 2 | Some slime |
| 5 | PG | Sample D, table 2 | Some slime |
| 6 | PG | Sample E, table 2 | Some slime |

The paint samples described above were also analyzed with respect to colour. The tinting strength was measured and analysed according to the "CIELAB" colour scale. In this scale a high L*value means that the colour is bright (white), a high positive a*value that the paint is red (negative value=green) and a high b*value that the paint is yellow (negative value=blue). Delta E is calculated as the distance in the colour scale from the white base, which was chosen as a reference. The results are given in table 5 below.

TABLE 5

| Sample | L* | a* | b* | deltaE |
|---|---|---|---|---|
| White base (Target) | 94.08 | −1.01 | 1–49 | — |
| Paint 1 | 90.32 | −0.84 | −0.15 | 4.11 |
| Paint 2 | 70.98 | 10.70 | −1.73 | 26.10 |
| Paint 3 | 87.72 | −0.41 | −1.59 | 7.10 |
| Paint 4 | 87.32 | 1.02 | −1.64 | 7.72 |
| Paint 5 | 88.82 | 0.75 | −1.06 | 6.10 |
| Paint 6 | 87.62 | 1.15 | −1.36 | 7.39 |

Table 5 shows that all paints based on granulated cuprous oxide have approximately the same or better low tint properties compared to LoLo Tint. Paint number 1 has better low tint properties than LoLo Tint.

According to FIG. 5 XLT-G gives at least as good results as LoLo Tint with respect to colour, while FIG. 6 shows that both Nordox PG and XLT-G gave similar or better results with respect to antifouling.

When all properties of interest are considered it can be concluded that the product according to the invention, XLT-G, gives better results than the two products in the present comparison, which must be considered as a non obvious technical advance Conclusions The examples above show that the invention, which is not influenced by solvents in the antifouling paints, is suitable for the preparation of copper oxide particles with a low tinting strength, has good antifouling properties, enables lowering of the copper contents in antifouling paints, making it possible to control the dissolution rate in water and resulting in superior handling properties.

What is claimed is:

1. A granulated copper oxide which is prepared by the granulation of a copper oxide slurry supplied with 0.3 to 8 percent binder which is resistant to organic solvents.

2. The granulated copper oxide of claim 1, wherein one or more organic polymer compounds are used as binders.

3. The granulated copper oxide of claim 2, wherein one or more polymer alcohols are used as binders.

4. The granulated copper oxide of claim 1, wherein polyvinyl alcohol (PVA) and/or polybutyl alcohol (PBA) are used as binders.

5. The granulated copper oxide of claim 1, having a medium particle size ($D_{50}$) in the range of 10–70 μm.

6. The granulated copper oxide of claim 1, having a medium primary particle size ($D_{50}$) in the range of 0.1–15 μm.

7. The granulated copper oxide of claim 1, having a bulk density in the range of 0.5–2,0 g/cm$^3$.

8. The process of preparing a granulated copper oxide according to claim 1, wherein primary particles of copper oxide are granulated together with an organic compound having a molecular weight in the range of 16,000–175,000 gram/mol as a binder.

9. The process of claim 8, wherein polyvinylalcohol (PVA) or polybutylalcohol (PVBA) is used as a binder.

10. The process of claim 8, wherein the granulation is effected in a spray dryer, preferably having a rotating matrix.

11. A process to prevent the deposition of organic material on a construction, comprising applying to a said construction a composition containing the granulated copper oxide of claim 1.

12. A process to prevent the deposition of organic material on a construction, comprising applying to a said construction a paint containing the granulated copper oxide of claim 1.

* * * * *